(12) United States Patent
Mirza et al.

(10) Patent No.: US 12,357,924 B2
(45) Date of Patent: Jul. 15, 2025

(54) **PROCESS FOR PRODUCING ENRICHED FRACTION FROM *BACOPA MONNIERI* EXTRACT FOR MANAGEMENT OF NEURODEGENERATIVE DISORDERS**

(71) Applicant: STAR HI HERBS PVT LTD, Karnakata (IN)

(72) Inventors: Firoz Hirehal Hussain Mirza, Karnakata (IN); Singam Setty Nanjundaiah, Karnakata (IN)

(73) Assignee: Star Hi Herbs Pvt Ltd., Karnakata (IN)

(*) Notice: Subject to any disclaimer, the term of this patent is extended or adjusted under 35 U.S.C. 154(b) by 737 days.

(21) Appl. No.: 17/570,918

(22) Filed: Jan. 7, 2022

(65) Prior Publication Data
US 2023/0047949 A1    Feb. 16, 2023

Related U.S. Application Data

(63) Continuation of application No. PCT/IB2021/059307, filed on Oct. 12, 2021.

(30) Foreign Application Priority Data

Aug. 13, 2021  (IN) .............................. 202141036735

(51) Int. Cl.
*A61K 36/28*     (2006.01)
*B01D 11/02*     (2006.01)

(52) U.S. Cl.
CPC ...... *B01D 11/0284* (2013.01); *B01D 11/0288* (2013.01); *B01D 11/0292* (2013.01); *A61K 36/28* (2013.01)

(58) Field of Classification Search
None
See application file for complete search history.

(56) References Cited

U.S. PATENT DOCUMENTS 6,833,143 B1    12/2004    Kahol et al.

FOREIGN PATENT DOCUMENTS

| AU | 2013354889 B2 | 7/2018 |
|---|---|---|
| WO | 2007/141807 A2 | 12/2007 |
| WO | WO-2017103831 A1 * | 6/2017 |

OTHER PUBLICATIONS

Gaidhani (Pharmacognosy Magazine (2009), vol. 5, No. 20 (suppl.) pp. 425-429).*

* cited by examiner

*Primary Examiner* — Susan Hoffman
(74) *Attorney, Agent, or Firm* — J. Peter Paredes; Amin Wasserman Gurnani LLP

(57) ABSTRACT

The present invention is the process of preparing enriched fraction of *Bacopa monnieri* extract Bacosane. *Bacopa monnieri* extract Bacosane is chemically standardized with 8 different bioactive compounds. The 8 bioactive compounds are asiatic acid, ebelin lactone, Bacogenin A1, bhramic acid, Bacoside A3, Bacopaside 1, Bacopaside 2 and jujubogenin. The process of preparing the *Bacopa monnieri* extract Bacosane is carried by extraction with ethanol, concentration, water washing, layer separation, extraction with ethyl acetate, concentration of ethyl acetate layer, water addition or IPA washing, spray drying or vacuum drying, milling, sieving, blending and packing of the resultant *Bacopa monnieri* extract Bacosane.

6 Claims, 9 Drawing Sheets

| Composition of Bacopa Monnieri extract Bacosane20% ||
|---|---|---|
| Compound | Observed value | Limit |
| Bacopaside 1 | 4.18 | NLT 2.0 |
| Bacoside A3 | 3.56 | NLT 2.0 |
| Bacopaside 2 | 5.07 | NLT 3.0 |
| Jujubogenin isomer | 4.79 | NLT 2.5 |
| Bacosaponine C | 3.38 | NLT 2.5 |
| Asiatic acid | 0.029 | NLT 0.01 |
| Bacogenin A1 | 0.19 | NLT 0.05 |
| Ebelin Lactone | 0.08 | NLT 0.01 |

Fig. 2

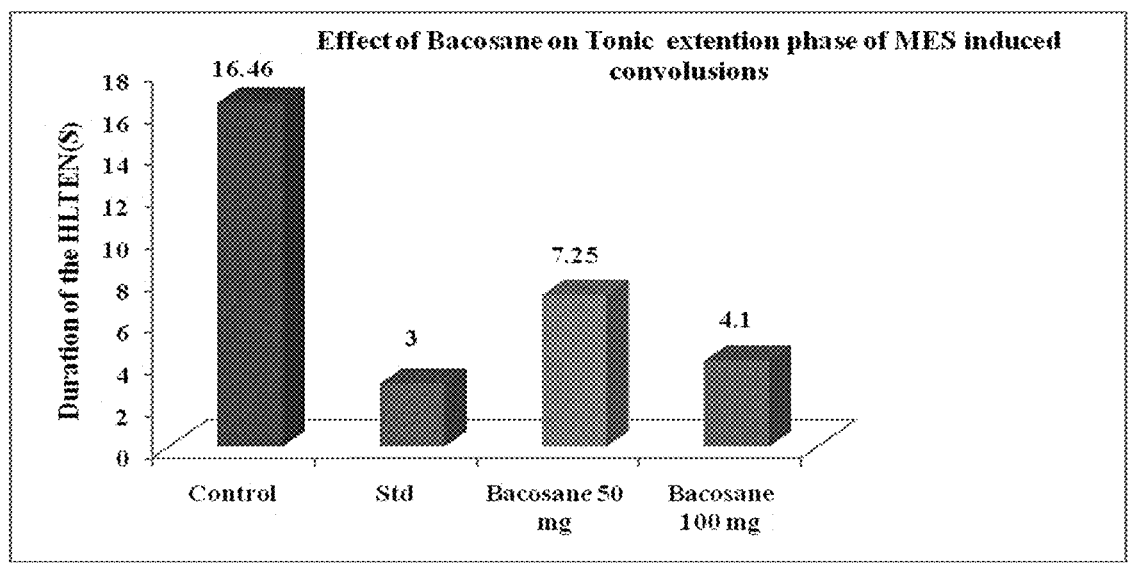

Fig. 3

| Treatment groups | Bacopa Monnieri extract Bacosane results of MES Induced seizure in (sec /min.) |||||
|---|---|---|---|---|---|
| | Flexion | Extension | Clonus | Stupor | Recover |
| Control | 10.42 | 16.46 | 17.48 | 37.89 | No recovery |
| Standard(Phenytoin) | 3.32 | 3.0 | 5.28 | 15.32 | 92.8 |
| (50 mg/kg)+PTZ | 8.18 | 7.25 | 10.32 | 25.76 | 145 |
| (100 mg/kg)+PTZ | 5.17 | 4.14 | 7.43 | 20.87 | 133 |

Fig. 4

| Treatment Groups | Latency (onset of clonic convulsion) sec/min | Onset of tonic Convulsion sec/min | Status of animal after 30min | |
|---|---|---|---|---|
| | | | No. of alive animals | % of Protection |
| Control (1% Na CMC) 10ml/kg P.O.) | 48.76 | 91.45 | 00 | 00 |
| (Phenytoin) 25mg/kg | 255.86 | 16 | All | 100 |
| Bacosane®50mg/kg | 74.34 | 42.65 | 4 | 66% |
| Bacosane®100mg/kg | 96.23 | 22.56 | 5 | 83% |

| SL. NO | Bacosane® | | Standard BHT | |
|---|---|---|---|---|
| | Bacopa Monnieri extract Bacosane (µg/ml) | % inhibition of Bacosane® | BHT (µg/ml) | % inhibition of BHT |
| 1 | 50 | 19.11 | Control | 0 |
| 2 | 100 | 32.69 | 20 | 10.11 |
| 3 | 150 | 56.03 | 40 | 25.69 |
| 4 | 200 | 66.7 | 60 | 38.03 |
| 5 | 250 | 77.6 | 80 | 45.07 |

Fig. 8

| Group and Dose (mg/kg, i.p) | Mean no. of entries in | | Mean time spent in (sec) | | Percentage of open arm entries | Percentage of time spent in open arm |
|---|---|---|---|---|---|---|
| | Open arm | Close arm | Open arm | Close arm | | |
| Vehicle (Normal saline) | 5.6±2.00 | 21.9±1.6 | 21.3±4.2 | 262.5±8.7 | 18.5±4.1 | 8.3±3.1 |
| Bacosane ® 50mg/kg | 12.1±1.6 | 11.8±1.3c | 43.6±4.5c | 135.4±6.9b | 49.21±2.8c | 26.3±4.2c |
| Bacosane ® 100mg/kg | 12.7±1.2b | 14.2±1.3b | 50.2±2.8c | 146.6±10.4a | 47.82±5.42c | 28.4±5.2c |
| Diazepam 1mg/kg | 12.7±1.2b | 14.1±.0.6b | 38.2±1.8a | 141.8±10.9a | 51.65±4.8c | 22.3±2.6c |

Fig. 9

| Groups | Locomotor activity |
|---|---|
| Group I Control | 301.50±43.67 |
| Group II STD (Diazepam) | 79.00±22.65 |
| Group III Bacopa Monnieri extract Bacosane(50mg/kg) | 158.17±12.35 |
| Group IV Bacopa Monnieri extract Bacosane(100mg/kg) | 110.83±33.04 |

Fig. 10

| Treatment (mg/kg,p.o) | No. of rearing | No. of assisted rearing | No. of square crossed |
|---|---|---|---|
| Vehicle (10ml/kg) | 9.2±1.2 | 20.0±2.8 | 127.3±6.2 |
| Diazepam (1mg/kg) | 15.9±1.7 | 32.8±4.2 | 178.3±6.9 |
| Bacopa Monnieri extract Bacosane50mg/kg | 15.9±1.7 | 32.6±3. | 185.5±6.9 |
| Bacopa Monnieri extract Bacosane100mg/kg | 16.5±1.7 | 35.7±1.6 | 197.9±10.7 |

Fig. 11

| Groups | Dose (mg/kg) | Latency time (s) | Transition number | Time spent in light compartment (s) |
|---|---|---|---|---|
| Control | ---------------- | 118.5±8.34 | 4.3±0.56 | 40.34±3.25 |
| Bacosane® | 50 | 185.8±4.9*** | 8.2±0.56** | 56.84±3,3* |
| Bacosane® | 100 | 178.4±10.34*** | 9.7±.78*** | 86.67±2.6*** |
| Diazepam | 1 | 61.56±4.6*** | 16.87±2.51*** | 105.54±7.32*** |

Fig. 12

| Organ | Control | Bacopa Monnieri extract Bacosane (5000 mg/kg) |
|---|---|---|
| Spleen | 0.36 ± 0.02 | 0.38 ± 0.02 ns |
| Liver | 3.36 ± 0.13 | 3.75 ± 0.24 ns |
| Lungs | 0.81 ± 0.05 | 0.80 ± 0.07 ns |
| Kidney | 0.86 ± 0.08 | 0.89 ± 0.04 ns |
| Heart | 0.47 ± 0.04 | 0.45 ± 0.03ns |

Fig. 13

| Parameter | Unit | Control | Bacopa Monnieri extract Bacosane(5000 mg/kg) |
|---|---|---|---|
| Haemoglobin (Hb) | g/L | 141.32 ± 3.11 | 141.65 ± 2.1 ns |
| Total red blood cells (RBC's) | $10^{12}$/L | 8.54 ± 0.23 | 8.71 ± 0.31 ns |
| Packed cell volume (PCV) | L/L | 0.63 ± 0.01 | 0.66 ± 0.00 ns |
| Mean corpuscular volume (MCV) | fL | 55.3 ± 0.00 | 55.21 ± 0.77 ns |
| Mean corpuscular haemoglobin (MCH) | pg | 18.58 ± 0.32 | 18.21 ± 0.5 ns |
| Mean corpuscular haemoglobin concentration (MCHC) | g/L | 327 ± 3.72 | 326.03 ± 3.13 ns |
| Total white blood cells (WBC's) | $10^9$/L | 7.62 ± 0.22 | 9.00 ± 2.4 ns |
| Neutrophils | % | 12.17 ± 1.03 | 12.13 ± 1.00 ns |
| Lymphocytes | % | 84.41 ± 1.43 | 81.02 ± 1.7 ns |
| Monocytes | % | 2.43 ± 0.00 | 2.54 ± 0.07 ns |
| Eosinophils | % | 1.03± 0.01 | 1.07 ± 0.02 ns |
| Platelet count | $10^9$/L | 872 ± 10.71 | 867.00 ± 17.11 ns |

Fig. 14

| Parameter | Unit | Control | Bacopa Monnieri extract Bacosane(5000mg/kg) |
|---|---|---|---|
| Sodium | mmol/L | 137.00± 0.10 | 137.20 ± 0.2 ns |
| Potassium | mmol/L | 6.18 ± 0.32 | 6.43 ± 0.23 ns |
| Chloride | mmol/L | 105.00 ± 0.62 | 105.40 ± 0.06 ns |
| Urea | mmol/L | 6.67 ± 0.34 | 6.46 ± 0.20 ns |
| Creatinine | μmol/L | 46.07 ± 0.36 | 46.12± 0.53 ns |
| Uric acid | mmol/L | 0.18 ± 0.03 | 0.19 ± 0.01 ns |
| Total protein | g/L | 68.34 ± 0.21 | 68.58 ± 0.43 ns |
| Albumin | g/L | 35.63 ± 0.67 | 36.13 ± 0.71 n |
| Globulin | g/L | 33.54 ± 0.47 | 33.60 ± 0.51 ns |
| Albumin/globulin ratio | | 1.18 ± 0.04 | 1.05 ± 0.05 ns |
| Alkaline phosphatase (ALP) | U/L | 134 ± 8.32 | 134.04 ± 7.0 ns |
| Aspartate aminotransferase (AST) | U/L | 73.26 ± 2.31 | 73.03 ± 2.39 ns |
| Alanine aminotransferase (ALT) | U/L | 46.41 ±0.71 | 46.81 ± 0.52 ns |

Fig. 15

| Group | Doses | Weight | | | |
|---|---|---|---|---|---|
| | | Initial day | 9th day | 18th day | 28th day |
| Control | - | 138.41±3.01 | 141.64 ± 2.31 | 149.45 ± 6.24 | 152.54 ± 3.85 |
| I | 250 mg/kg | 142.23±7.22 | 148.24 ± 2.53 | 152.71 ± 3.21 | 156.72 ± 2.74 |
| II | 500 mg/kg | 144.22 ± 6.24 | 150.19 ± 6.01 | 155.81 ± 5.89 | 160.87 ± 8.81 |
| III | 1000 mg/k g | 142.25 ± 3.22 | 147.28 ± 3.89 | 152.52 ± 4.86 | 159.28 ± 4.01 |

Fig. 16

| Organs | Control | Bacopa Monnieri extract Bacosane(250 mg/kg) | Bacopa Monnieri extract Bacosane(500 mg/kg) | Bacopa Monnieri extract Bacosane(1000 mg/kg) |
|---|---|---|---|---|
| Spleen | 0.39 ± 0.02 | 0.38 ± 0.01 ns | 0.32 ± 0.02 ns | 0.33 ± 0.01 ns |
| Liver | 3.08 ± 0.17 | 3.85 ± 0.26 ns | 3.67 ± 0.04 ns | 3.18 ± 0.08 ns |
| Lungs | 0.84 ± 0.06 | 0.90 ± 0.09 ns | 0.83 ± 0.02 ns | 0.86 ± 0.01 ns |
| Kidney | 0.76 ± 0.02 | 0.79 ± 0.01 ns | 0.75 ± 0.01 ns | 0.77 ± 0.03 ns |
| Heart | 0.48 ± 0.02 | 0.47 ± 0.01 ns | 0.44 ± 0.01 ns | 0.45 ± 0.02 ns |

Fig. 17

| Parameter | Unit | Control | 250mg/kg | 500 mg/kg | 1000 mg/kg |
|---|---|---|---|---|---|
| Haemoglobin (Hb.) | g/L | 151.33 ± 0.45 | 147.11 ± 0.32 | 148.31 ± 0.54 | 150.52 ± 0.92 |
| Total red blood cells (RBC's) | $10^{12}$/L | 7.83 ± 0.78 | 7.86 ± 0.81 ns | 7.38 ± 0.36 ns | 7.95 ± 0.43 ns |
| Total white blood cells (WBC's) | $10^9$/L | 7.82 ± 0.17 | 7.91 ± 0.11 ns | 7.45 ± 0.19 ns | 7.83 ± 0.39 ns |
| Red blood cell distribution unit (RDW) | % | 14.25 ± 1.12 | 13.21 ± 1.93 ns | 13.53 ± 1.10 ns | 13.34 ± 1.09 ns |
| Mean corpuscular haemoglobin (MCH) | pg | 17.18 ± 0.17 | 17.93 ± 0.22 ns | 17.33 ± 0.14 ns | 17.47 ± 0.24 ns |
| Mean corpuscular haemoglobin (MCH) | pg | 17.18 ± 0.17 | 17.93 ± 0.22 ns | 17.33 ± 0.14 ns | 17.47 ± 0.24 ns |
| Mean platelet volume (MPV) | fL | 7.65 ± 0.04 | 7.34 ± 0.08 ns | 7.17 ± 0.01 ns | 7.38 ± 0.01 ns |
| Mean corpuscular volume (MCV) | fL | 55.41 ± 0.77 | 54.33 ± 0.21 ns | 54.81 ± 0.11 ns | 55.01 ± 0.03 ns |
| Packed cell volume (PCV) | L/L | 0.48 ± 0.01 | 0.45 ± 0.07 ns | 0.47 ± 0.02 ns | 0.44 ± 0.01 ns |
| Platelet count | $10^9$/L | 834.60 ± 48.20 | 839.51 ± 42.31 ns | 842.11 ± 41.11 ns | 842.08 ± 29.3 ns |
| Lymphocytes | % | 85.11 ± 2.61 | 85.00 ± 2.81 ns | 85.51 ± 1.33 ns | 85.33 ± 1.00 ns |
| Neutrophils | % | 12.88 ± 1.01 | 12.74 ± 1.13 ns | 12.98 ± 1.11 ns | 12.20 ± 1.79 ns |
| Monocytes | % | 2.16 ± 0.04 | 2.83 ± 0.11 ns | 2.71 ± 0.65 ns | 2.97 ± 0.31 ns |
| Procalcitonin (PCT) | % | 0.99 ± 0.23 | 0.75 ± 0.37 ns | 0.68 ± 0.41 ns | 0.64 ± 0.44 ns |
| Red blood cell distribution unit (RDW) | % | 14.37 ± 1.12 | 13.11 ± 1.93 ns | 13.49 ± 1.10 ns | 13.33 ± 1.09 ns |
| Platelet distribution width (PDW) | fL | 11.5 ± 0.01 | 10.91 ± 0.01 ns | 10.59 ± 0.04 ns | 9.76 ± 0.07 ns |
| Platelet large cell ratio (P-LCR) | % | 14.51 ± 0.11 | 14.70 ± 0.22 ns | 13.01 ± 0.22 ns | 13.71 ± 0.23 ns |

Fig. 18

| Parameter | Unit | Control | 250mg/kg | 500 mg/kg | 1000 mg/kg |
|---|---|---|---|---|---|
| Chloride | mmol/L | 101.83 ± 0.03 | 101.70 ± 0.05 ns | 101.11 ± 0.03 ns | 100.00 ± 0.01 ns |
| Potassium | mmol/L | 6.28 ± 0.01 | 6.73 ± 0.09 ns | 6.49 ± 0.04 ns | 6.88 ± 0.13 ns |
| Uric acid | mmol/L | 0.18 ± 0.04 | 0.17 ± 0.01 ns | 0.15 ± 0.09 ns | 0.16 ± 0.02 ns |
| Urea | mmol/L | 6.75 ± 0.21 | 6.34 ± 0.17 ns | 6.68 ± 0.18 ns | 6.76 ± 0.10 ns |
| Sodium | mmol/L | 134.00 ± 0.44 | 132.20 ± 0.94 ns | 131.70 ± 0.86 ns | 132.30 ± 0.56 ns |
| Creatinine | μmol/L | 48.30 ± 0.52 | 43.17 ± 0.69 ns | 45.1 ± 0.61 ns | 45.79 ± 0.49 ns |
| Albumin | g/L | 34.68 ± 0.03 | 35.21 ± 0.03 ns | 36.77 ± 0.01 ns | 39.92 ± 0.03 ns |
| Total protein | g/L | 67.50 ± 0.90 | 67.30 ± 0.86 ns | 68.00 ± 1.14 ns | 69.81 ± 0.90 ns |
| globulin | g/L | 32.83 ± 0.05 | 32.09 ± 0.09 ns | 31.23 ± 0.09 ns | 28.89 ± 0.07 ns |
| AST | U/L | 72.00 ± 6.91 | 75.00 ± 6.93 ns | 76.21 ± 7.89 ns | 78.00 ± 6.34 ns |
| ALT | U/L | 50.67 ± 1.17 | 46.21 ± 2.82 ns | 50.21 ± 2.41 ns | 52.00 ± 1.53 ns |
| Alkaline phosphatase (ALP) | U/L | 133.83 ± 6.17 | 134.70 ± 10.12 ns | 135.65 ± 12.92 ns | 135.00 ± 11.33 ns |
| Bilirubin (Total) | mg/dL | 0.39 ± 0.01 | 0.35 ± 0.00 ns | 0.39 ± 0.01 ns | 0.49 ± 0.32 ns |

Fig. 19

PROCESS FOR PRODUCING ENRICHED FRACTION FROM *BACOPA MONNIERI* EXTRACT FOR MANAGEMENT OF NEURODEGENERATIVE DISORDERS

CROSS REFERENCE TO RELATED APPLICATIONS

The present application is a continuation and claims priority to PCT Application Serial No: PCT/IB2021/059307, filed Oct. 12, 2021, which claims priority to Indian Application Serial No. 202141036735, filed Aug. 13, 2021, all herein incorporated by reference in their entireties.

DESCRIPTION OF THE INVENTION

Technical Field of the Invention

The invention is related to the field of preparation of novel anti-stress, nutritional supplement formulation with neuro-support factors intended for the sustenance of optimal healthy mental cognition. More particularly, the invention relates to a process for preparation of enriched fraction of *Bacopa monnieri* extract for the treatment of neurodegenerative disorders.

BACKGROUND OF THE INVENTION

Optimal cognitive functions such as attention, working memory and management function, are central to performance in many sports. Aging is accompanied by a decline in episodic memory performance seen in middle aged reputed as occurring in almost half the population aged over 65 years. There are three main forms of memory loss, based on the severity, viz., Age Associated Memory Impairment (AAMI), Mild Cognitive Impairment (CMI) and Dementia, in the ascending order. Dementia is characterized by decline, fragility, vulnerability, a loss of the most important cognitive functions and even a loss of self. One's mental capacity to think and reason is directly handled by memory. Losing control over the cognitive functions will adversely affect one's self-esteem, productivity and well-being.

Other reasons for decline in memory performance especially in middle aged persons is usage of drugs like Anti-depression (TCAs) drugs which are prescribed for depression, anxiety disorders, eating disorders, obsessive-compulsive disorder, chronic pain, smoking cessation and some hormone-mediated disorders, such as severe menstrual cramps and hot flashes. About 35 percent of adults taking TCAs report some degree of memory impairment and about 54 percent report having difficulty in concentrating. TCAs are thought to cause memory problems by blocking the action of serotonin and norepinephrine two of the brain's key chemical messengers. For most stimulant medications, the most common side effect is their addition potential. Many youngsters in particular tend to get addicted to amphetamines for their CNS stimulating effects.

Over the last decade there has been increasing attention in research to try to identify preventive strategies to slow the progression of AAMI and age-related cognitive decline, thereby identifying the tools that may delay the onset of dementia. The pharmaceutical companies are investigating multiple compounds to develop memory boosting "cognitive enhancers" that can prevent cognitive decline and preserve the ability to remember. Nootropics are also called as smart drugs, memory enhancers, neuro enhancers or cognitive enhancers. However, it is observed that these drugs have side effects and cause loss or deterioration of the brain function in the long run. There have been reports disclosing serious adverse effects and toxicity in individuals administered with nootropic drugs. In some cases, an addiction to the nootropic drugs is also reported. Side effects may include gastrointestinal discomfort, insomnia, blurry vision, high blood pressure, a fast heart rate, circulation problems, and addiction. The other side effects are loss of appetite, headaches, restlessness, or tremor; anxiety or nervousness; dizziness, dryness of the mouth or an unpleasant taste in the mouth; diarrhea or constipation; or impotence or change in sex drive, stomachaches, blood pressure problems in those with a history of hypertension and nervousness or who consume excessive caffeine and have anxiety. The incidence of side effects can vary widely among the different ADHD medications.

There are also variety of "brain boosters", most want studies to back their memory-enhancing claims. Consumption of a number of plant-derived phytochemicals can modulate these psychological parameters, although there is a scarcity of sporting proof. The structural groups into which these phytochemicals belong vary in terms of the ecological roles they play for the plant, their toxicity and the extent to which they work on brain function.

In past few decades, inventors have surprisingly discovered that extract of *Bacopa monnieri* acutely enhance cognitive performance in humans who are mentally stressed, mentally fatigued and cognitively challenged. *Bacopa monnieri* has been used in traditional Ayurvedic medicine for its claimed anti-amnesic, sedative, memory enhancing, anti-epileptic and anxiolytic effects for thousands of years.

*Bacopa monnieri* (Linn.) Pennell, family Scrophulariaceae, is an indigenous plant, found throughout India, Nepal, Sri Lanka, China, Taiwan, Vietnam, Florida, Hawaii, and some other southern states of USA. *Bacopa monnieri*, popularly known as Brahmi, has been traditionally used in Ayurveda since ages for its memory enhancing properties. *Bacopa monnieri* is used in indigenous systems of medicine for the treatment of various nervous system ailments such as insomnia, anxiety, epilepsy, and hysteria. It is believed that the components of *Bacopa monnieri* extract which help in repair of damaged neurons, neuronal synthesis, and the restoration of synaptic activity, and also innerve impulse transmission. *Bacopa monnieri* also demonstrates stress-decreasing activity in both acute and chronic stress situations. Anxiety is a psychological state, and it is characterized by somatic, emotional, cognitive, and behavioral components, associated with significant disorder.

The Patent Application WO2007141807 titled "*A synergistic herbal composition from bacopa species for management of neurodegenerative disorders and a process of preparation thereof*" discloses a potent synergistic herbal composition [BacoMind®] from the plant species *Bacopa monnieri* and its beneficial effects in learning, memory, cognition, and attention deficit hyperactivity disorder [ADHD] or attention deficit disorder [ADD]. In addition, the present invention provides the synergistic composition derived from *Bacopa monnieri* such that the resulting composition consists of Bacoside A3 in the range of 0.1 to 25%, Bacopaside II in the range of 0.1 to 25%, Jujubogenin isomer of Bacopasaponin C in the range of 0.1 to 25%, Bacopasaponin C in the range of 0.1 to 25%, Bacopaside I in the range of 0.1 to 25%, Bacosine in the range of 0.1 to 25%, Apigenin in the range of 0.05 to 5%, Luteolin in the range of 0.05 to 5% and Sitosterol-D-glucoside in the range of 0.05 to 5% constituting up to 50% by weight of the total composition.

The Patent Application AU2013354889B2 titled "Uses of *Bacopa monnieri* extract" discloses a method for acutely improving/enhancing cognitive performance in a human subject, wherein the subject is mentally stressed, mentally fatigued and/or cognitively challenged, the method comprising administration to the subject of an extract of *Bacopa monnieri*, wherein the subject is mentally stressed, mentally fatigued and/or cognitively challenged as a result of undergoing a test, examination or some other activity involving cognition, wherein the extract is administered up to 3 hours prior to the subject undergoing the test, examination or other activity involving cognition, and wherein the extract is administered in an amount of at least about 320 mg.

The Patent Application U.S. Pat. No. 6,833,143 titled "Process for the preparation of a extract rich in bacosides from the herb *Bacopa monnieri*" discloses a novel process for the preparation of bacosides enriched fraction in a non-hygroscopic form the extract of *Bacopa monnieri*, the said process comprising the steps of drying freshly harvested herb in a hot air oven at 37-42° C., powdering and sieving the dried herb to obtain powder of 30-40 mesh size, defatting the powdered herb with hexane in a modified soxhlet extractor, extracting the defatted powdered herb with acetone, again extracting the same herb with methanol to obtain an extract containing bacosides, concentrating the extract to one twentieth of its original volume under reduced pressure, gradually adding the concentrated extract to acetone for precipitating the bacosides, filtering the bacosides in a Nutsche type vacuum filter, dissolving the crude bacoside mass into 2-10 parts water, extracting the bacoside solution with n-butanol to selectively transfer the bacosides to the solvent phase, separating and concentrating the solvent phase under vacuum to obtain semi-dry mass, dissolving the semi dried mass into 2-10 parts water, adding and stirring 1-5% of β-cyclodextrin to stabilize the bacosides, spray drying the stabilized bacoside solution by maintaining hot air temperature at 90-110° C., to obtain a stable free flowing fraction of *Bacopa monnieri* rich in bacosides.

There is a need for a process of preparation of *Bacopa monnieri* extract for treatment of neurodegenerative disorders, which can improve and enhance cognitive performance with minimum or no side effects on the health.

SUMMARY OF THE INVENTION

The following presents a simplified summary of the disclosure in order to provide a basic understanding. This summary is not an extensive overview of the disclosure, and it does not identify key/critical elements of the invention or delineate the scope of the invention. Its sole purpose is to present some concepts disclosed herein in a simplified form as a prelude to the more detailed description that is presented later.

The object of the present invention is to provide a process for the preparation of herbal composition in such a manner that it contains a predetermined amount of bioactive compounds.

It is yet another object of the present invention to provide process for producing compositions for the structural/functional nutritional support for those who struggle with poor focus, concentration, and memory.

It is yet another object of the present invention to provide compositions comprising nutritional factors helpful to those who subjectively experience transient mental fatigue or poor cognitive function.

It is yet another object of the present invention to acutely improve and enhance cognitive performance in a human subject when the use of an extract of *Bacopa monnieri* in accordance with the process of the present invention.

*Bacopa monnieri* has widely been used in herbal nutraceuticals for supporting brain and nerve function, enhancing memory, alertness and mental concentration. *Bacopa monnieri* extract are also proven to be effective for the treatment of behavioral disorders, anxiety and conditions, where anxiety may play a role such as irritable bowel syndrome. The compounds responsible for the pharmacological effects of *Bacopa monnieri* include alkaloids, saponins and sterols. All the available products containing the extract of *Bacopa Monnieri* are standardized to the content of Bacoside A, Bacoside B and Bacosides.

The present invention is a process of preparation of enhanced fraction of *Bacopa monnieri* extract to formulate *Bacopa Monnieri* extract Bacosane. *Bacopa Monnieri* extract Bacosane is chemically standardized with 8 different bioactive compounds such as asiatic acid, ebelin lactone, Bacogenin A1, bhramic acid, Bacoside A3, Bacopaside 1, Bacopaside 2 and jujubogenin. Thus, *Bacopa Monnieri* extract Bacosane shows enhanced neuroprotective activity naturally without any side-effects. The *Bacopa Monnieri* extract Bacosane is found to be safe in regulatory pharmacological and toxicological studies. No contraindications or cautions associated with *Bacopa Monnieri* extract Bacosane have been reported. It was observed that the medicinal quality of the *Bacopa Monnieri* extract Bacosane preparations depends upon the presence and quality of enriched saponins.

In accordance with an aspect of the present invention sub-chronic and chronic administration of asiatic acid (30 mg/kg) has been shown to increase cell proliferation in the hippocampus and stimulate spatial working memory. Asiatic acid is well known to enhance learning and memory, which are associated with hippocampus neurogenesis. The increased percentage of bacosides protects the brain against oxidative damage and age-related cognitive deterioration with several mechanisms of action.

In accordance with the aspect of the present invention bhramic acid is well known antioxidant activity and very good anti-stress agents thus act as well-known anti-depressant without/with least side effects.

In accordance with the aspect of the present invention, the synergistic composition of *Bacopa Monnieri* extract Bacosane is useful in enhancing anti-stress, cognition, improving learning and memory in slow learners and management of neuro-degenerative disorders.

In accordance with the aspect of the present invention, *Bacopa Monnieri* extract Bacosane is used for sports medicine, mood disorders, improving short term memory, long term memory and attention span, by exerting its effect on increasing concentration ability, speech & recall defects and improving overall mental performance. *Bacopa Monnieri* extract Bacosane has significant effect on relieving the fatigue and providing the movement function which is expected to have beneficial effect as sports medicine.

BRIEF DESCRIPTION OF THE DRAWINGS

These features and advantages of the present disclosure may be appreciated by reviewing the following description of the present disclosure, along with the accompanying figures wherein like reference numerals refer to like parts.

FIG. 2 depicts the composition of *Bacopa Monnieri* extract Bacosane 20% of concentration.

FIG. 3 depicts graphical representation of effect of *Bacopa Monnieri* extract Bacosane on tonic extension phase in maximal electroshock seizure (MES) model.

FIG. 4 depicts *Bacopa Monnieri* extract Bacosane results of MES induced seizure in (sec/min).

FIG. 8 depicts free radical scavenging activity of *Bacopa Monnieri* extract Bacosane using 1, 1-diphenyl-2-picrylhydrazil (DPPH).

FIG. 9 depicts comparison of *Bacopa Monnieri* extract Bacosane and diazepam in behavior of rats in elevated plus maze test.

FIG. 10 depicts the effects of *Bacopa Monnieri* extract Bacosane in Actophotometer method.

FIG. 11 depicts comparison of effect of *Bacopa Monnieri* extract Bacosane and Diazepam in behavior of rats in open field test.

FIG. 12 depicts the effects of repeated administration of *Bacopa Monnieri* extract Bacosane in the light-dark transition test on rats.

FIG. 13 depicts relative organ weight of rats treated with a single dose of *Bacopa Monnieri* extract Bacosane for 14 days.

FIG. 14 depicts the effect of *Bacopa Monnieri* extract Bacosane on haematological parameters in acute oral toxicity analysis.

FIG. 15 depicts the effect of *Bacopa Monnieri* extract Bacosane on biochemical parameters in acute oral toxicity analysis.

FIG. 16 depicts the effect of *Bacopa Monnieri* extract Bacosane on body weight of rats (g) at different days.

FIG. 17 depicts the relative organ weight of rats treated with different doses of *Bacopa Monnieri* extract Bacosane for 28 days.

FIG. 18 depicts the effect of *Bacopa Monnieri* extract Bacosane on haematological parameters in the sub-acute oral toxicity analysis.

FIG. 19 depicts the effect of *Bacopa Monnieri* extract Bacosane on biochemical parameters in the sub-acute oral toxicity analysis.

DETAILED DESCRIPTION OF THE INVENTION

Figure 1:
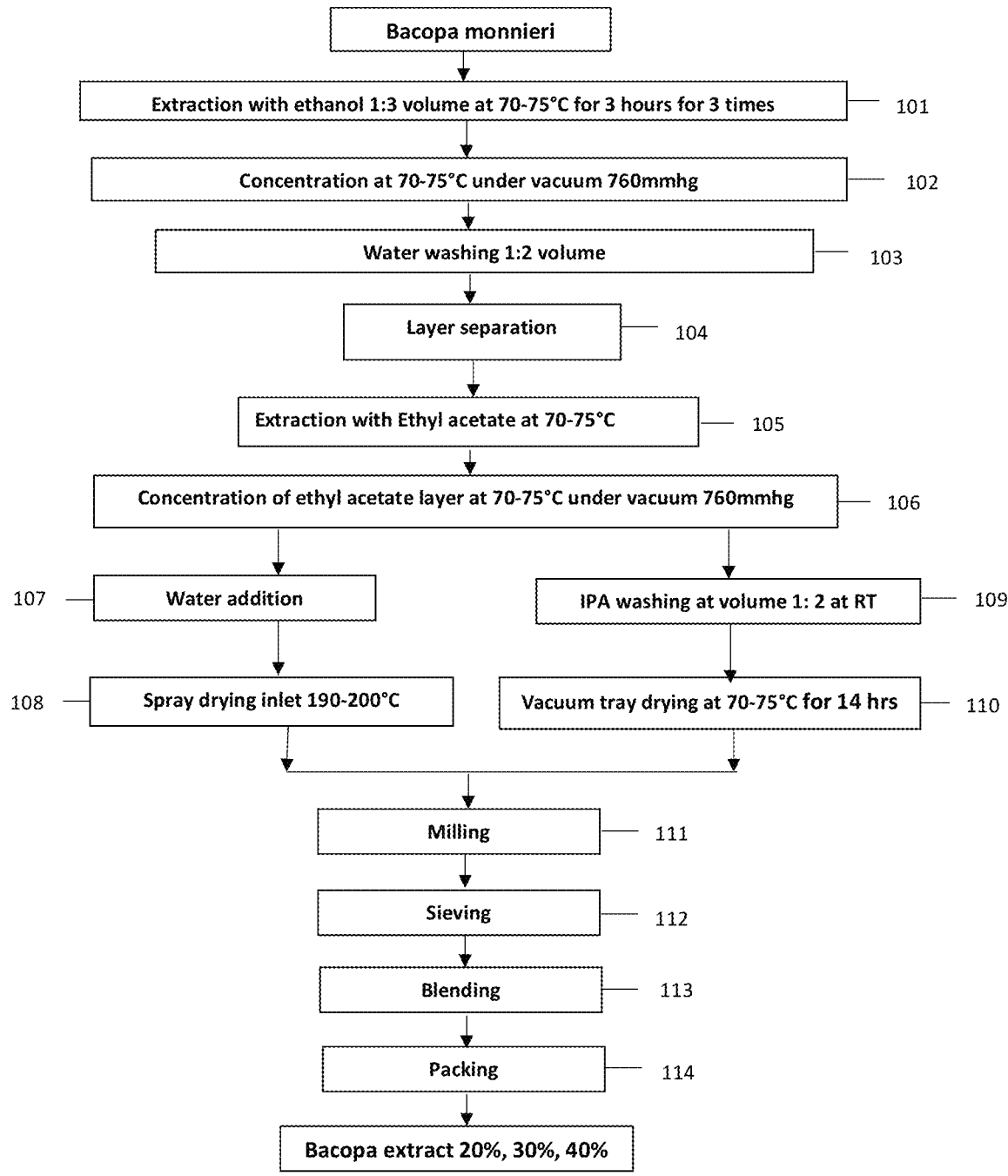
FIG. 1 depicts the process flow of the process of producing enriched fraction from *Bacopa monnieri* extract in accordance with the present invention.

The present disclosure is best understood with reference to the detailed figures and description set forth herein. Various embodiments have been discussed with reference to the figures. However, those skilled in the art will readily appreciate that the detailed descriptions provided herein with respect to the figures are merely for explanatory purposes, as the methods or process and systems may extend beyond the described embodiments. As used in the description herein and throughout the claims that follow, the meaning of "a," "an," and "the" includes plural reference unless the context dictates otherwise. Also, as used in the description herein, the meaning of "in" includes "in" and "on" unless the context dictates otherwise.

References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

Recitation of ranges of values herein are merely intended to serve as a shorthand method of referring individually to each separate value falling within the range, unless otherwise indicated herein, and each separate value is incorporated into the specification as if it were individually recited herein. The word "about," when accompanying a numerical value, is to be construed as indicating a deviation of up to and inclusive of 10% from the stated numerical value. The use of any and all examples, or exemplary language ("e.g." or "such as") provided herein, is intended merely to better illuminate the invention and does not pose a limitation on the scope of the invention unless otherwise claimed. No language in the specification should be construed as indicating any nonclaimed element as essential to the practice of the invention.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

In an exemplary embodiment of the present invention, the process of preparing enriched fraction of *Bacopa monnieri* extract resulting in formulation of *Bacopa monnieri* extract Bacosane which is chemically standardized with 8 different bioactive compounds. The 8 bioactive compounds are asiatic acid, ebelin lactone, Bacogenin A1, bhramic acid, Bacoside A3, Bacopaside 1, Bacopaside 2 and jujubogenin.

In accordance with an exemplary embodiment of the present invention sub-chronic and chronic administration of asiatic acid (30 mg/kg) has been shown to increase cell proliferation in the hippocampus and stimulate spatial working memory. Asiatic acid is well known to enhance learning and memory, which are associated with hippocampus neurogenesis. The increased percentage of bacosides protects the brain against oxidative damage and age-related cognitive deterioration with several mechanisms of action.

In accordance with an exemplary embodiment of the present invention bhramic acid is well known antioxidant activity and very good anti-stress agents thus act as well-known anti-depressant without/with least side effects.

In accordance with the exemplary embodiment of the present invention, process of preparing enriched fraction of *Bacopa monnieri* extract comprising the steps of as shown in FIG. 1:

a) extracting *Bacopa monnieri* with ethanol (101) at volume 1:3 at temperature of 70-75° C. for duration of 3 hours, repeated 3 times;

b) concentrating (102) the mixture from step (a) at temperature of 70-75° C. under vacuum 760 mmhg;

c) water washing (103) the concentrated mixture from step (b) at volume 1:2;

d) performing layer separation (104) of the mixture from step (c);

e) extracting the mixture from step (d) with Ethyl acetate (105) at temperature of 70-75° C.;

f) concentrating (106) the mixture from step (e) at temperature of 70-75° C. under vacuum 760 mmhg;

g) adding water (107) to the concentrated mixture from step (f);

h) spray drying (108) the mixture from step (g) at 190-200° C.;

i) milling (111) the dried mixture from step (h);

j) sieving the mixture (112);

k) blending the mixture (113); and l) packing (114) the resultant composition of *Bacopa monnieri* extract.

In accordance with the exemplary embodiment of the present invention the resultant composition of *Bacopa monnieri* extract Bacosane can be of 20%, 30%, 40% concentration. FIG. 2 depicts the composition of *Bacopa monnieri* extract Bacosane 20% which comprises bioactive components such as 8 bioactive compounds are asiatic acid, ebelin lactone, Bacogenin A1, bhramic acid, Bacoside A3, Bacopaside 1, Bacopaside 2 and jujubogenin. The resultant composition comprising at least a therapeutically sufficient amount of the *Bacopa monnieri* extract Bacosane as active ingredient and a pharmaceutically acceptable vehicle or carrier.

In an alternate embodiment of the present invention, after concentrating (106) the mixture from step (e) at temperature of 70-75° C. under vacuum 760 mmhg; such concentrated mixture from step (f) can be washed with isopropyl Alcohol (109) at 1:2 volume at room temperature.

In accordance with the alternate embodiment of the present invention, after the concentrated mixture from step (f) is washed with isopropyl alcohol (*Bacopa monnieri*) it can undergo vacuum tray drying (110) at 70-75° C. for 14 hours.

In accordance with the alternate embodiment of the present invention, the resultant composition of *Bacopa monnieri* extract Bacosane can be of 20%, 30%, 40% concentration. The *Bacopa monnieri* extract Bacosane 20% comprises bioactive components such as 8 bioactive compounds are asiatic acid, ebelin lactone, bacogenin A1, bhramic acid, bacoside A3, bacopaside 1, bacopaside 2 and jujubogenin. The resultant composition comprising at least a therapeutically sufficient amount of the *Bacopa monnieri* extract Bacosane as active ingredient and a pharmaceutically acceptable vehicle or carrier.

In further embodiment of the present invention the concentration of bacogenin A1 and ebelin lactone in *Bacopa monnieri* extract Bacosane is determined by High Pressure Liquid Chromatography (HPLC) which is conducted by quality control chemists. The compounds required to determine the estimation of Bacogenin A1 and Ebelin Lactone are Acetonitrile HPLC grade, Water HPLC grade, Methanol HPLC grade. The process is conducted by mixing HPLC grade methanol and water in the ratio 70:30, filtering and degas the mixture. A flow rate is 1.0 ml per minute in column C18, of 250 mmX4.6 mm, 5)µ with the end capped and base deactivated is observed at conditions like temperature of 27±1° C. and detector of UV at 278 nm.

In further embodiment of the present invention the concentration of bacosides and asiatic acid in *Bacopa monnieri* extract Bacosane is determined by High Pressure Liquid Chromatography (HPLC) conducted by quality control chemists. The compounds required to determine the estimation of Bacosides, and Asiatic acid are Potassium dihydrogen phosphate, Acetonitrile HPLC grade, Water HPLC grade, Methanol HPLC grade. The process to determine the concentration of bacosides and asiatic acid in *Bacopa monnieri* extract Bacosane comprises of two phases: Mobile Phase A and Mobile Phase B.

Mobile phase A includes dissolving of 0.1 g of anhydrous potassium dihydrogen phosphate in 900 ml of water, adding 0.5 ml of Phosphoric acid. This mixture is diluted to 1000 ml with water mix, followed by filtering and degassing the mixture.

Mobile phase B includes filtering of mixture with Acetonitrile and degassing the mixture.

The following examples are offered to illustrate various aspects of the invention. However, the examples are not intended to limit or define the scope of the invention in any manner.

Example 1: The Anticonvulsant Activity of *Bacopa monnieri* Extract Bacosane in Maximal Electroshock Seizure (MES) Models In further embodiment of the present invention the anticonvulsant activity of *Bacopa monnieri* extract Bacosane is determined using Pentylenetetrazole (PTZ) and the maximal electroshock seizure (MES) models. The analysis is performed on healthy Swiss mice of either sex, weighing about 25-30 g and Wistar rats of either sex, weighing about 150-200 g. The animals were grouped and housed in polyacrylic cages (38×23×10 cm) with not more than six animals per cage and maintained under standard laboratory conditions (temperature 25° C.) with dark and light cycle (12/12 h). All the animals were acclimatized to laboratory condition for a week before commencement of the analysis. The animals were randomly allocated into four groups of six each: Group I (control group), Group II, Group III, Group IV.

Group-I received 10 ml/kg of 1% NaCMC p.o. which served as control.

Group-II received phenytoin sodium (25 mg/kg, orally) as standard controls in MES method and PTZ induced seizures method respectively.

Group-III and IV were administered two graded doses of *Bacopa monnieri* extract Bacosane i.e., 50 mg/kg and 100 mg/kg, respectively, p.o.

In the above analysis the percentage protection of animals was recorded as percentage of reduction in duration of seizures wherein the control group is assumed as 100%. The observations of group II, III and IV were compared with control Group-I. It is observed that *Bacopa monnieri* extract Bacosane has potential anticonvulsant activity due to the presence of certain active phytoconstituents. The anticonvulsant activity of *Bacopa monnieri* extract Bacosane involves GABAergic transmission and glutaminergic transmission or sodium channel blockage. However, it can be considered that the *Bacopa monnieri* extract Bacosane as a potent anticonvulsant supplement. The analysis and observations of Pentylenetetrazole (PTZ) and the maximal electroshock seizure (MES) models is shown in FIG. 3 to FIG. 6.

FIG. 3 is the graphical representation of effect of *Bacopa Monnieri* extract Bacosane on tonic extension phase in MES induced convulsion. The result is obtained through Maximal electroshock induced seizures (MES) induced in albino Wister rats where twenty-four male rats were allotted into four groups of six animals each. After a pre-treatment time of 30 minutes, the seizures were induced by maximal electroshock with the help of electroconvulsiometer by passing current of 50 mA for 0.2 sec using corneal electrodes. A drop of electrolyte solution 0.9% sodium chloride with lignocaine was applied to the corneal electrodes, which ensures better contact and the mortality rate to zero. The applied current intensity elicited complete tonic extension of the hind limbs in control rats. The rats were observed for 2 minutes, wherein the rats were placed in a clear rectangular polypropylene cage with an open top, permitting full view of the animal motor responses to record the pilot analysis of various phases of convulsions, like tonic flexion, extension, stupor and mortality due to convulsions.

FIG. 4 shows the observed and recorded values of the effect of *Bacopa Monnieri* extract Bacosane on tonic extension phase in MES induced convulsion in (sec/min) value. In MES model, two different w/w ratio doses of *Bacopa Monnieri* extract Bacosane of 50 mg/kg and 100 mg/kg were administered daily once for 7 days to group III and IV respectively. It was found that lower (50 mg/kg) and higher (100 mg/kg) dose of Bacosane had produced a significant anticonvulsant effect in various phases of convolutions as shown in FIG. 4. The *Bacopa Monnieri* extract Bacosane exhibited a dose dependent reduction in various phases of epileptic seizure in comparison with the control group. There was also a significant reduction in the time required for the righting reflex (recovery) in the Bacosane treated groups compared with control group. It is also observed that Phenytoin and different doses of *Bacopa Monnieri* extract Bacosane decreased hind limb tonic extension as compared to control group. It is observed that the standard drug Phenytoin showed 100% protection in animals against MES and it also abolished the extensor phase completely.

Figures 5, 6:
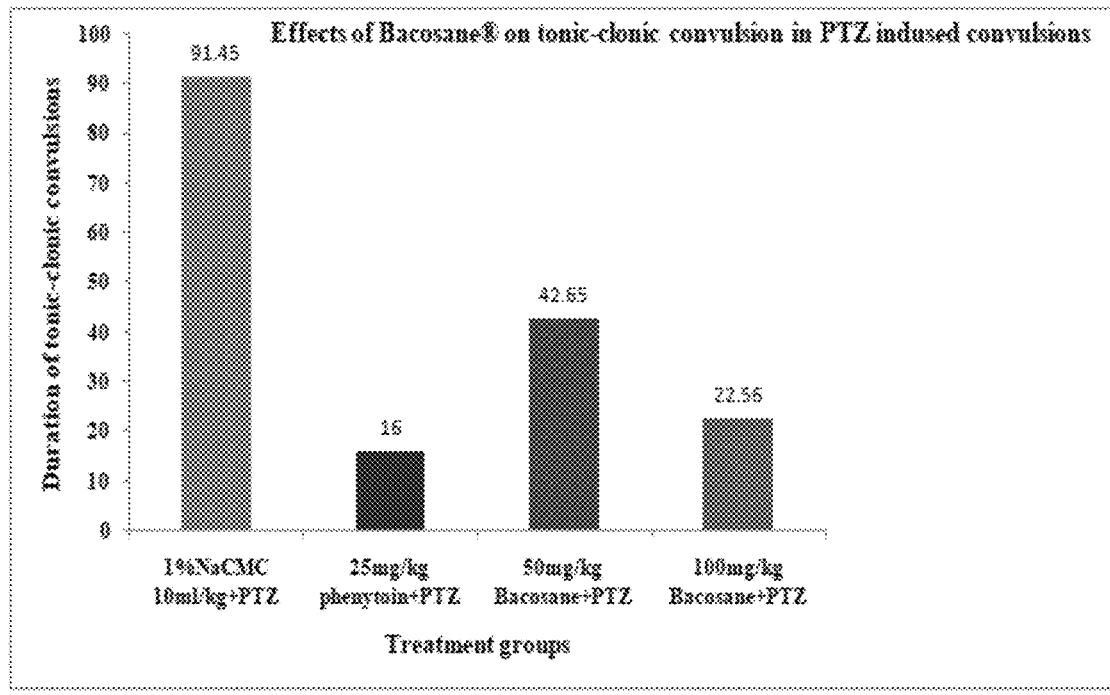
FIG. 5 depicts graphical representation of effect of *Bacopa Monnieri* extract Bacosane on tonic-clonic convolution in Pentylenetetrazole (PTZ) induced convolutions model.
FIG. 6 depicts *Bacopa Monnieri* extract Bacosane results of PTZ induced convulsions model.

FIG. 5 depicts graphical representation of effect of *Bacopa Monnieri* extract Bacosane on tonic-clonic convolution in Pentylenetetrazole (PTZ) induced model in rats. The depicted result in FIG. 5 is obtained from the analysis, which is conducted on twenty-four rats which were allotted into four groups (as mentioned earlier) of six animals each. The test animals' group III and group IV (n=6) received 50 mg/kg and 100 mg/kg of *Bacopa Monnieri* extract Bacosane orally, wherein the suspension is prepared in 1% sodium CMC solution; and standard group received phenytoin sodium (25 mg/kg) orally in the form of suspension. After a pre-treatment time of 60 minutes, PTZ (90 mg/kg i.p.) was administered to the four groups of animals. PTZ at the dose of 90 mg/kg i.p. was injected to induce tonic-clonic convulsions in rats. The onset of convulsions, number of animals that convulsed and number of animals that were protected from clonic convulsions were recorded.

FIG. 6 depicts the observed results of effect of *Bacopa Monnieri* extract Bacosane in PTZ induced convulsions model. It is observed that 50 mg/kg and 100 mg/kg of *Bacopa Monnieri* extract Bacosane exhibited a significant anticonvulsant effect by increasing latency, onset of clonic convulsions and decreases onset of tonic seizures. After, 30 minutes of interval, 67% and 84% of animals survived at a dose of 50 mg/kg and 100 mg/kg respectively. It is observed that intraperitoneal (IP) administration of PTZ induced tonic-clonic convulsions with 100% mortality in the control group. It was found that lower (50 mg/kg) and higher (1000 mg/kg) dose of *Bacopa Monnieri* extract Bacosane had produced a significant delayed the onset of clones as compared to the control group. It is also observed that the standard drug Phenytoin sodium had exhibited significantly anticonvulsant activity and gave 100% protection.

Example 2: The Antioxidant Activity of *Bacopa monnieri* Extract In Vitro

In further embodiment of the present invention, the antioxidant activity of *Bacopa Monnieri* extract Bacosane is determined by employing in vitro methods, such as free radical scavenging activity using 1, 1-diphenyl-2-picrylhydrazil (DPPH) and observed result is compared with antioxidant activity of standard butylated hydroxytoluene (BHT). The observed antioxidant activity of *Bacopa monnieri* extract Bacosane and BHT is observed and compared as depicted in FIGS. 7A-7B and FIG. 8.

Figure 7A:
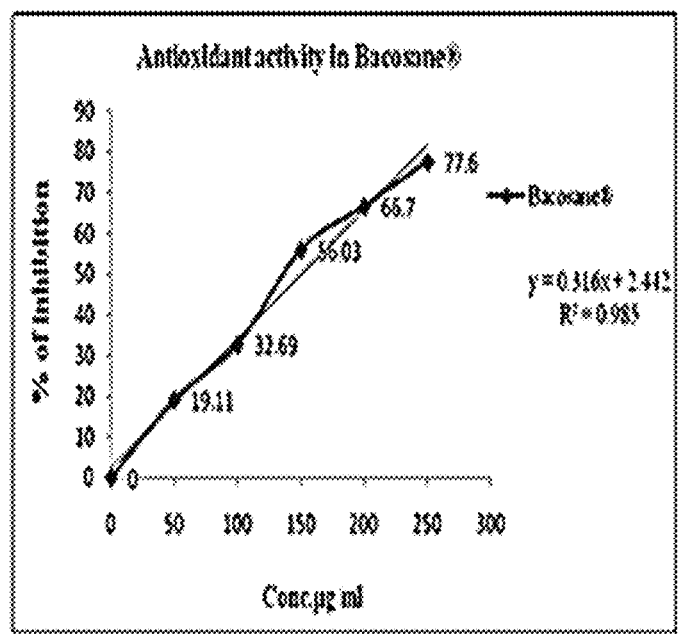
FIGS. 7A-7B depicts percentage of inhibition in 1,1-diphenyl-2-picrylhydrazil (DPPH) in free radical scavenging assay.
Figure 7B:
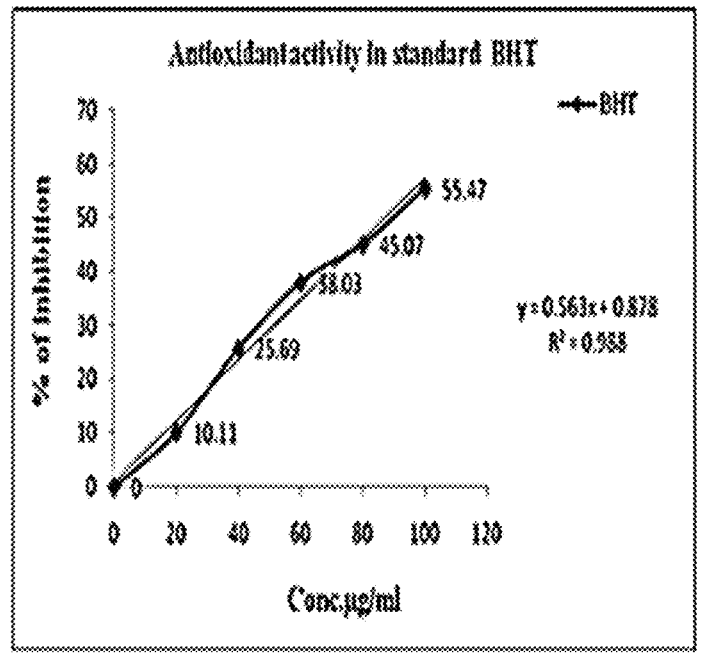

FIGS. 7A-7B depicts percentage of inhibition of 1, 1-diphenyl-2-picrylhydrazil (DPPH) in free radical scavenging assay. The free radical scavenging activity of *Bacopa monnieri* extract Bacosane and BHT is determined through the process comprising steps of: preparing solution of 0.1 mM DPPH in methanol, and 1.5 mL of this solution was mixed with 1.5 mL of extract in methanol at different concentrations (50, 100, 150, 200 and 250 m/mL); and measuring the absorbance at 517 nm, after leaving the above mixture for 30 minutes of incubation at dark room. Butylated hydroxytoluene (BHT) was used as the reference standard at different concentrations (20, 40, 60, 80 and 100 m/m1). The radical scavenging activity of DPPH was calculated using the following equation: $[A_0-A_1]/A_0 \times 100$ where $A_0$ is the absorbance of the control, and $A_1$ is the absorbance of the standard. Then the percentage (%) of inhibition was plotted against concentration of the *Bacopa monnieri* extract Bacosane and BHT, and from the graph as shown in FIGS. 7A-7B half-maximal inhibitory concentration (IC50) was calculated to determine the efficacy of *Bacopa monnieri* extract Bacosane in comparison to standard butylated hydroxytoluene (BHT).

FIG. 8 depicts the observed results from the analysis of antioxidant activity of *Bacopa monnieri* extract and BHT by employing free radical scavenging activity through inhibition of 1, 1-diphenyl-2-picrylhydrazil (DPPH). The observed values of half-maximal inhibitory concentration (IC50 of *Bacopa monnieri* extract Bacosane and standard butylated hydroxytoluene (BHT) are 87.25 μg/ml and 150.50 μg/ml respectively. The results obtained in the present analysis indicate that *Bacopa monnieri* extract Bacosane exhibits strong free radicals scavenging activity. The overall antioxidant activity of *Bacopa monnieri* extract might be attributed to its polyphenolic content, triterpenoids and flavonoids. However, from the observed results of the above activity it can be suggested that *Bacopa monnieri* could be a potential source of natural antioxidant that could have great importance as therapeutic agents in preventing or slowing the progress of aging and age associated oxidative stress related degenerative diseases.

Example 3: The Anxiolytic Activity of *Bacopa monnieri* Extract In Vitro

In further embodiment of the present invention the anxiolytic effect of *Bacopa monnieri* extract Bacosane is determined by employing 4 different tests i.e., the elevated plus maze (EPM) test, open field test (OFT), Astrophotometer test and Light dark transition test. The compounds used in these four tests comprises *Bacopa monnieri* extract Bacosane; and Diazepam (1 mg/kg, i.p.) which is used as standard anxiolytic agent. The four tests are performed on Wistar strain rats of both sex of weighing 130 to 180 g, which were divided into four groups of six rats each (Group I, Group II, Group III and Group IV)

Group I vehicle (normal saline) at a dose of 10 ml/kg body weight

Group II received *Bacopa monnieri* extract Bacosane, at a dose of 50 mg/kg body weight Group III received *Bacopa monnieri* extract Bacosane, at a dose of 100 mg/kg body weight Group IV received standard drug, diazepam 1 mg/kg body weight The method employed and the results from the four test (as mentioned earlier) are shown in FIG. 9-FIG. 12. It is also observed from the above four tests that there no significant decrease in locomotor activity in the animals tested. From these results, it can be concluded that *Bacopa monnieri* extract Bacosane has a great potential for anxiolytic activity when compared against standard drug diazepam. The *Bacopa monnieri* extract Bacosane can be considered as central depressant, or it may be used in variety of painful and excitatory conditions.

FIG. 9 depicts comparison of effect of *Bacopa monnieri* extract Bacosane and diazepam in behavior of rats in elevated plus maze test. In elevated plus maze test after 1 h of oral administration of vehicle (normal saline), diazepam and *Bacopa monnieri* extract Bacosane were administered to Group II and Group III, IV respectively. The elevated plus-maze apparatus consists of two opposite open arms (16 cm×5 cm), crossed with two closed arms of same dimensions with 25 cm high wall. The arms are connected with Central Square (7 cm×7 cm). In the plus maze test, the rats were individually placed on the central platform facing towards open arm. The percentage of time spent (duration) in open arms and frequency of open arm entries were counted for a period of 5 minutes. During 5 minutes test period the following measures are taken: the number of entries into the open arm; the number of entries into the closed arm; time spent in the open arm; time spent in the closed arm (as shown in FIG. 9). The percentage of time spent in the open arms and number of open arm entries were calculated using the formulas [100×open/(open+enclosed)] and (100×open/total entries), respectively.

From the observed results (values are represented in Mean±SEM) in FIG. 9 it is observed that the vehicle (normal saline) treated rats spent more time in closed arm and showed less entries in open arm compared to closed arm of the maze during the 5 minutes test period. It is also observed that rats treated with diazepam showed significant increase in the percentage of open arms entries as well as time spent in open arm whereas, in closed arm number of entries and time spent were significantly decreased. It is observed that the administration of *Bacopa monnieri* extract Bacosane (50 and 100 mg/kg, p.o,) exhibited significant increase in the percentage of number of open arm entries and time spent in open arm whereas, in the closed arm number of entries and time spent was significantly reduced as compared to vehicle-treated group.

FIG. 10 depicts the effects of *Bacopa monnieri* extract Bacosane in actophotometer method. In this test, the rats are placed in the digital Actophotometer in which a constant beam of light from six lights will be made to fall on corresponding photoelectric cells. The photoelectric cells get activated when an animal crosses the beam of light and thereby cuts off (crossing) the rays of light falling on it. After 1 hour of *Bacopa Monnieri* extract Bacosane administration the numbers of crossings are counted for a period of 10 minutes by the actophotometer. The number of crossings was taken as a parameter of the locomotor activity of the rats. From the observed results (values are represented in Mean±SEM) in FIG. 10 it can be derived that the Standard drug Diazepam significantly reduced the number of crossings of light beams when compared to control group locomotor activity (301.50±43.67). Animals treated with low dose of *Bacopa monnieri* extract Bacosane of 50 mg/kg showed greater decrease in locomotor activity (158.17±12.35) than animals treated with high dose of *Bacopa monnieri* extract Bacosane of 100 mg/kg (110.83±33.04). The reduction in locomotor activity with 50 mg/kg and 100 mg/kg of *Bacopa monnieri* extract Bacosane showed a statistically significant dose-dependent anxiolytic effect.

FIG. 11 depicts comparison of effect of *Bacopa monnieri* extract Bacosane and Diazepam on behavior of rats in open field test. The apparatus comprises a wooden box (60×60×60 cm). The area of the open field was divided into 16 squares (15×15 cm), the four inner squares in the center and 12 squares in the periphery along the walls. The other identical condition comprises of sound attenuated and dark experimental room. The open field arena was illuminated with a 40-W lamp, focusing on the field from a height of about 75-100 cm. After 1 hour of oral administration of vehicle (normal saline), diazepam and *Bacopa monnieri* extract Bacosane the animals were placed individually in one of the corner squares and number of rearing, assisted rearing and number of squares crossed were observed for the period of 5 minutes. From the observed results (values are represented in Mean±SEM) in FIG. 11 it can be derived that the Diazepam (1 mg/kg) and *Bacopa monnieri* extract Bacosane (50 mg/kg and 100 mg/kg i.p) administered groups significantly exhibited anxiolysis which can be evidenced by increased ambulation, rearing and preening and decreased defecations compared to group administered control (normal saline).

FIG. 12 depicts the effects of repeated administration of *Bacopa monnieri* extract Bacosane on the light-dark transition test with rats. The light/dark box (45×27×27 cm) is used which is made from plywood and it consisted of two chambers that are connected by an opening (7.5×7.5 cm) located at the floor level in the center of the dividing wall. The floor was divided into 9×9 cm squares and was covered with Plexiglas. The small chamber (18×27 cm) was painted black and the larger chamber (27×27 cm) was painted white. A bright illumination was provided by a 60 watt table lamp located 40 cm above the center of the white chamber. Rats were injected (i.p) with *Bacopa monnieri* extract Bacosane once per day for 7 days. The test was performed 1 hour after the last administration of *Bacopa monnieri* extract Bacosane. The standard drug diazepam (i.p.) was given once 30 minutes before the test. During the test, the rats were placed at the center of the light compartment with their back to the dark compartment, and then transition behavior of the rats is observed and recorded for over 10 minutes. The parameters recorded include the latency time (latency before entering the dark compartment), the transition number (the number of dark compartments to light compartment transitions), and the total time spent visiting the light compartment. From the observed results (values are represented in Mean±SEM) of FIG. 12 it can be derived that the group administered with *Bacopa monnieri* extract Bacosane (50 and 100 mg/kg, p.o.) showed a significant increase in the latency time to enter into dark compartment, increase in number of crossings, and increase in time spent in light box in comparison with the group administered with vehicle (normal saline).

Example 4: The Toxicity of *Bacopa monnieri* Extract In Vitro

In further embodiment of the present invention, the acute and subacute toxicity is determined in experimental rats which are induced by standardized *Bacopa monnieri* extract Bacosane. The experimental animals used for these tests are male and female albino rats (Rattus norvegicus) weighing 130-160 g. The animals were grouped and housed in polyacrylic cages (38×23×10 cm) with not more than six animals per cage and maintained under standard laboratory conditions (temperature 25° c.) with dark and light cycle (12/12 h). All the animals were acclimatized to laboratory condition for a week before commencement of experiment. The parameters observed in both acute and sub-acute tests are body weight of the rats, relative organ weights in the rats, haematological parameters and biochemical parameters. The observations and results of the acute and sub-acute toxicity in the experimental rats are shown in FIG. 13-19.

In further embodiment of the present invention the acute toxicity is determined by performing toxicity test on rats of both sexes aged 6-8 weeks old which are fasted for 16 hours. *Bacopa monnieri* extract Bacosane was dissolved in 10% Tween 20 and administered only once orally at a single dose of 5000 mg/kg at a rate of 20 mL/kg to both the sexes of rats (n=12; six males, six females), whereas the control group only received 10% Tween 20 as a vehicle. The rats are allowed free access to food and water and observed for 24 hours after administration of the extract, and a special care is given during first 4 hours. The visual observations such as mortality, various changes in physical appearance, behaviour (salivation, lethargy), and any injury or illness were observed and recorded once daily for 14 days.

FIG. 13 depicts relative organ weight of rats treated with a single dose of *Bacopa monnieri* extract Bacosane for 14 days during analysis of acute toxicity in the rats. On 15th day the treated rats were then euthanized through intraperitoneal injection of ketamine. The organs, namely the liver, heart, spleen, lung, and kidney, were carefully excised and weighed. It is observed that single administration of *Bacopa monnieri* extract Bacosane at a dose of 5000 mg/kg produced no toxic effect on the behavioral responses of the rats that are observed for 14 days. There were no signs of changes in the behaviour patterns, skin, eyes, salivation, and diarrhea of the rats. Neither mortality nor significant weight loss was observed. From the observed results (values are represented in Mean±SEM) in FIG. 13 it can be derived that there is no significant differences observed in the relative organ weight between *Bacopa Monnieri* extract Bacosane administered group and control group.

FIG. 14 depicts the effect of *Bacopa monnieri* extract Bacosane on haematological parameters in acute oral toxicity analysis. The visual observations such as mortality, various changes in physical appearance, behaviour (salivation, lethargy), and any injury or illness were observed and recorded for the group of rats administered with *Bacopa monnieri* extract Bacosane once daily for 14 days. On the 15th day, blood samples of this group of rats were collected into EDTA containing tubes for haematological analysis. From the observed results (values are represented in Mean±SEM) in FIG. 14 it can be derived that there was no significant change in the haematological parameters in the *Bacopa monnieri* extract Bacosane administered group compared to control group. The differences appeared only in two treated rats.

FIG. 15 depicts the effect of *Bacopa monnieri* extract Bacosane on biochemical parameters in acute oral toxicity analysis. The visual observations such as mortality, various changes in physical appearance, behaviour (salivation, lethargy), and any injury or illness were observed and recorded for the group of rats administered with *Bacopa Monnieri* extract Bacosane once daily for 14 days. On the 15th day, blood samples of this group of rats were collected by cardiac puncture into non-heparinized tubes for biochemical analysis. From the observed results (values are represented in Mean±SEM) of FIG. 15 it can be derived that there was no significant change in the biochemical parameters in the *Bacopa monnieri* extract Bacosane administered group compared to control group. The differences appeared only in two treated rats.

In further embodiment of the present invention the sub-acute toxicity analysis of *Bacopa monnieri* extract Bacosane is determined for the doses of w/w ratio of 250, 500, and 1000 mg/kg body weight. Four groups: group I (control), Group II, III and IV (administered dose of 250, 500, and 1000 mg/kg of *Bacopa monnieri* extract Bacosane respectively), at every 24 hours for 28 days and control group received 10% Tween 20 as a vehicle at the same volume. Various toxic signs and observation, such as body weight, mortality, and food and water intake were monitored daily for 28 days. The amount of food and water consumed was measured, their residue was calculated the next day to obtain the difference, which was recorded as daily food (g/rat/day) and water use (ml/rat/day). It is observed from the results that the daily oral administration of *Bacopa monnieri* extract Bacosane for 28 days did not produce any symptoms of toxicity in rats, including the highest dose tested at 1000 mg/kg body weight. It is also observed that no deaths or obvious clinical signs were found in any groups throughout the analysis of sub-acute toxicity. It is also observed that none of the rats showed signs of toxicity in their skin, fur, eyes, sleep, salivation, diarrhea, and behaviour.

FIG. 16 depicts the effect of *Bacopa monnieri* extract Bacosane on body weight of rats (g) at different days. A weekly body weight was determined on initial (0) day, 9th, 18th, and 28th days of four groups. From the observed results (values are represented in Mean±SEM) of FIG. 16 it can be derived that there is no significant changes in the body weight are observed in group II, III and IV in comparison with Group I (control).

FIG. 17 depicts the relative organ weight of rats treated with different doses of *Bacopa monnieri* extract Bacosane for 28 days. The sub-acute toxicity analysis of *Bacopa monnieri* extract Bacosane is determined for the doses of w/w ratio of 250, 500, and 1000 mg/kg body weight. Four groups: group I (control), Group II, III and IV (administered dose of 250, 500, and 1000 mg/kg of *Bacopa monnieri* extract Bacosane respectively), at every 24 hours for 28 days and control group received 10% Tween 20 as a vehicle at the same volume. Various toxic signs and observation, such as body weight, mortality, and food and water intake were monitored daily for 28 days. After 28 days, the survived rats were then euthanized after blood collection and the internal organs (heart, liver, spleen, kidney, and lungs) were removed and weighed to determine the relative organ weights and observed for any gross lesions. From the observed results (values are represented in Mean±SEM) of FIG. 17 it can be derived that the relative organ weight of each organ recorded at necropsy in the treatment groups II, III and IV did not show a significant difference as compared to control group I.

FIG. 18 depicts the effect of *Bacopa monnieri* extract Bacosane on haematological parameters in the sub-acute oral toxicity analysis. The four groups of rats are monitored for 28 days for various toxic signs and observations, such as body weight, mortality, and food and water intake. Blood samples (1.5 ml) of four groups were obtained into heparinized tubes after 14 days and 28 days from the retro-orbital area of the rats to calculate haematological parameters. The haematological parameters, like haemoglobin (Hb), red blood cell (RBC), PCV (packed cell volume), MCV (mean corpuscular volume), mean corpuscular haemoglobin (MCH), mean corpuscular haemoglobin concentration (MCHC), total white blood cells (WBCs), differential WBCs (neutrophil, lymphocyte, and monocyte), platelet count, red blood cell distribution unit (RDW), platelet distribution width (PDW), platelet large cell ratio (P-LCR), mean platelet volume (MPV), and procalcitonin (PCT) were estimated. From the observed results (values are represented in Mean±SEM) of FIG. 18 it can be derived that the effect of subacute administration of *Bacopa monnieri* extract Bacosane on haematological parameters for group II, III and IV were not significantly different from the control group I.

FIG. 19 depicts the effect of *Bacopa monnieri* extract Bacosane on biochemical parameters in the sub-acute oral toxicity analysis. The four groups of rats are monitored for 28 days for various toxic signs and observations, such as body weight, mortality, and food and water intake. Blood samples (1.5 ml) of four groups were obtained into dry tubes after 14 days and 28 days from the retro-orbital area of the rats to calculate biochemical (dry tubes) parameters. Dry tubes carrying blood collected for investigation were centrifuged at 3000 rpm at 25° C. for 15 minutes to get the serum, which was stored at −20° C. for the analysis of biochemical parameters. The parameters such as aspartate aminotransferase (AST), alanine aminotransferase (ALT) and ALP are very important for a liver function test. Serum urea and creatinine, (sodium, potassium, chloride, uric acid, Total protein, Albumin/globulin ratio, albumin, globulin and bilirubin are the most important parameters for the assessment of kidney function. From the observed results (values are represented in Mean±SEM) of FIG. 19 it can be derived that the results in group II, III and IV showed no significant variations in AST, ALT, ALP, urea, sodium, potassium, chloride, uric acid, total protein, albumin/globulin ratio, albumin and globulin, creatinine and bilirubin at each trial dose, in comparison with the control group I.

The *Bacopa monnieri* extract Bacosane is found to be safe in regulatory pharmacological and toxicological studies. No contraindications or cautions associated with *Bacopa monnieri* extract Bacosane have been reported. It was observed that the medicinal quality of the *Bacopa monnieri* extract Bacosane preparations depends upon the presence and quality of enriched saponins.

In accordance with an embodiment of the present invention the synergistic composition of *Bacopa monnieri* extract Bacosane is useful in enhancing anti-stress, cognition, improving learning and memory in slow learners and management of neuro-degenerative disorders.

In accordance with an embodiment of the present invention *Bacopa monnieri* extract Bacosane is used for sports medicine, mood disorders, improving short term memory, long term memory and attention span, by exerting its effect on increasing concentration ability, speech & recall defects and improving overall mental performance. *Bacopa monnieri* extract Bacosane has significant effect on relieving the fatigue and providing the movement function which is expected to have beneficial effect as sports medicine.

All publications and patent applications mentioned in this specification are herein incorporated by reference to the same extent as if each individual publication or patent application was specifically and individually indicated to be incorporated by reference.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

We claim:

1. A process of preparation of enriched *Bacopa monnieri* extract, such said process comprising steps of:
   a. extracting *Bacopa monnieri* with ethanol (101) at volume 1:3 at temperature of 70-75° C. for duration of 3 hours, repeated 3 times;
   b. concentrating (102) the ethanol *Bacopa monnieri* extract at temperature of 70-75° C. under vacuum 760 mmhg;
   c. water washing (103) the concentrated *Bacopa monnieri* at volume 1:2 and separating a layer of concentrated *Bacopa monnieri* (104) from water;
   d. extracting the separated layer containing *Bacopa monnieri* with Ethyl acetate (105) at temperature of 70-75° C.;
   e. concentrating (106) the ethyl acetate *Bacopa monnieri* extract at temperature of 70-75° C. under vacuum 760 mmhg;
   f. washing the concentrated extract followed by drying;
   g. milling (111) the dried extract followed by sieving (112) and blending the *Bacopa monnieri* extract (113) followed by packing (114) an enriched *Bacopa monnieri* extract.

2. The process as claimed in claim 1, wherein washing of concentrated extract from step (f) requires adding water (107) and drying the extract is carried in spray drying inlet (108) at 190-200° C.

3. The process as claimed in claim 1, wherein the concentrated extract from step (f) is washed using Isopropyl alcohol (IPA) at 1:2 volume at room temperature (109) and the washed extract is dried through vacuum tray drying (110) at 70-75° C. for 14 hours.

4. The process as claimed in claim 1, wherein the concentration of the *Bacopa monnieri* extract, is 20%.

5. The process as claimed in claim 1, wherein the enriched *Bacopa monnieri* extract comprises asiatic acid, ebelin lactone, bacogenin A1, brahmic acid, bacoside A3, bacopaside 1, bacopaside 2 and Jujubogenin.

6. The process as claimed in claim 1, wherein the bioactive components of the enriched *Bacopa monnieri* extract enhances anti-stress, bioavailability, antioxidant activity, and mental health cognition.

* * * * *